United States Patent
Boyd et al.

(10) Patent No.: US 9,402,963 B2
(45) Date of Patent: Aug. 2, 2016

(54) MEDICATED MODULE WITH DUAL SAFETY GUARDS

(75) Inventors: Malcolm Stanley Boyd, Warwickshire (GB); James Alexander Davies, Warwickshire (GB); Naceur Rekaya, Warwickshire (GB)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 993 days.

(21) Appl. No.: 13/576,701

(22) PCT Filed: Feb. 1, 2011

(86) PCT No.: PCT/EP2011/051395
§ 371 (c)(1),
(2), (4) Date: Dec. 17, 2012

(87) PCT Pub. No.: WO2011/095480
PCT Pub. Date: Aug. 11, 2011

(65) Prior Publication Data
US 2013/0079724 A1    Mar. 28, 2013

(30) Foreign Application Priority Data
Apr. 23, 2010    (EP) .................................... 10160839

(51) Int. Cl.
*A61M 5/32*    (2006.01)
*A61M 5/24*    (2006.01)
(Continued)

(52) U.S. Cl.
CPC .......... *A61M 5/3202* (2013.01); *A61M 5/2448* (2013.01); *A61M 5/284* (2013.01);
(Continued)

(58) Field of Classification Search
CPC . A61M 5/2066; A61M 5/2448; A61M 5/284; A61M 5/3146; A61M 5/3202; A61M 5/3287; A61M 5/288; A61M 5/31525; A61M 5/3155; A61M 5/3294; A61M 5/326; A61M 2005/1787; A61M 2005/3247; A61M 2005/3267; A61M 2205/583
USPC .............................................. 604/198, 82–88
See application file for complete search history.

(56) References Cited

U.S. PATENT DOCUMENTS

| 4,518,384 A | 5/1985 | Tarello et al. |
| 6,562,002 B1 | 5/2003 | Taylor |

(Continued)

FOREIGN PATENT DOCUMENTS

| DE | 102006041809 | 3/2008 |
| EP | 1685865 | 8/2006 |

(Continued)

OTHER PUBLICATIONS

International Preliminary Report on Patentability for Int. App. No. PCT/EP2011/051395, mailed Aug. 16, 2012.
(Continued)

*Primary Examiner* — Edelmira Bosques
*Assistant Examiner* — Leah Swanson
(74) *Attorney, Agent, or Firm* — McDonnell Boehnen Hulbert & Berghoff LLP (57) ABSTRACT

A medicated module for an injection system to co-deliver at least two medicaments is disclosed, where a drug delivery device containing a primary medicament accepts a medicated module containing a single dose of a second medicament and where both medicaments are delivered through a single hollow needle. The medicated module comprises two housings removably connected to each other, where each housing contains a sterile needle and needle guard assembly that locks out after the needle is inserted in an injection site.

15 Claims, 4 Drawing Sheets

(51) Int. Cl.
*A61M 5/28* (2006.01)
*A61M 5/31* (2006.01)
*A61M 5/315* (2006.01)
*A61M 5/34* (2006.01)
*A61M 5/178* (2006.01)

(52) U.S. Cl.
CPC .......... *A61M 5/3129* (2013.01); *A61M 5/3146* (2013.01); *A61M 5/326* (2013.01); *A61M 5/288* (2013.01); *A61M 5/3155* (2013.01); *A61M 5/31525* (2013.01); *A61M 5/3294* (2013.01); *A61M 5/3297* (2013.01); *A61M 5/347* (2013.01); *A61M 2005/1787* (2013.01); *A61M 2005/3247* (2013.01); *A61M 2005/3267* (2013.01); *A61M 2205/583* (2013.01)

(56) References Cited

U.S. PATENT DOCUMENTS 7,850,648 B2    12/2010  Gratwohl et al.
2003/0105430 A1*  6/2003  Lavi ................... A61M 5/2033
                                                        604/136
2006/0229562 A1* 10/2006  Marsh .................. A61M 5/204
                                                       604/164.01
2006/0276755 A1  12/2006  Sullivan et al.
2007/0225640 A1*  9/2007  Chang ............... A61M 5/31596
                                                         604/92
2009/0018506 A1   1/2009  Daily et al.

FOREIGN PATENT DOCUMENTS

JP       H09-51947         2/1997
JP       2007-511299       5/2007
WO    WO 2008137578 A1 * 11/2008 ........... A61M 5/284

OTHER PUBLICATIONS

International Search Report and Written Opinion for Int. App. No. PCT/EP2011/051395, mailed May 10, 2011.

Japanese Office Action for JP App. No. 2012-551594, mailed Nov. 11, 2014.

* cited by examiner

MEDICATED MODULE WITH DUAL SAFETY GUARDS

CROSS REFERENCE TO RELATED APPLICATIONS

The present application is a U.S. National Phase Application pursuant to 35 U.S.C. §371 of International Application No. PCT/EP2011/051395 filed Feb. 1, 2011, which claims priority to U.S. Provisional Patent Application No. 61/301,710 filed on Feb. 5, 2010 and European Patent Application No. 10160839.6 filed Apr. 23, 2010. The entire disclosure contents of these applications are herewith incorporated by reference into the present application.

FIELD OF INVENTION

Specific embodiments of this disclosure relate to medical devices and methods of delivering at least two drug agents from separate reservoirs using devices having only a single dose setting mechanism and a single dispense interface. A single delivery procedure initiated by the user causes a, preferably, non-user settable dose of a second drug agent and a, preferably, variable set dose of a first drug agent to be delivered to the patient. The drug agents may be available in two or more reservoirs, containers or packages, each containing independent (single drug compound) or pre-mixed (co-formulated multiple drug compounds) drug agents. Specifically, our disclosure concerns a medicated module that has two safety guard assemblies. Each safety guard assembly may comprise lock out features where a first portion of the module containing the first guard can be removed by a user to expose a second injection needle and guard assembly. The present disclosure is of particular benefit where the therapeutic response can be optimized for a specific target patient group, through control and definition of the therapeutic profile.

BACKGROUND

Certain disease states require treatment using one or more different medicaments. Some drug compounds need to be delivered in a specific relationship with each other in order to deliver the optimum therapeutic dose. Here, combination therapy may be desirable, but not possible in a single formulation for reasons such as, but not limited to, stability, compromised therapeutic performance and toxicology.

For example, in some cases it might be beneficial to treat a diabetic with a long acting insulin and with a glucagon-like peptide-1 (GLP-1), which is derived from the transcription product of the proglucagon gene. GLP-1 is found in the body and is secreted by the intestinal L cell as a gut hormone. GLP-1 possesses several physiological properties that make it (and its analogs) a subject of intensive investigation as a potential treatment of diabetes mellitus.

There are a number of potential problems when delivering two active medicaments or "agents" simultaneously. The two active agents may interact with each other during the long-term, shelf life storage of the formulation. Therefore, it is advantageous to store the active components separately and only combine them at the point of delivery, e.g. injection, needle-less injection, pumps, or inhalation. However, the process for combining the two agents needs to be simple and convenient for the user to perform reliably, repeatedly and safely.

A further problem is that the quantities and/or proportions of each active agent making up the combination therapy may need to be varied for each user or at different stages of their therapy. For example one or more actives may require a titration period to gradually introduce a patient up to a "maintenance" dose. A further example would be if one active requires a non-adjustable fixed dose while the other is varied in response to a patient's symptoms or physical condition. This problem means that pre-mixed formulations of multiple active agents may not be suitable as these pre-mixed formulations would have a fixed ratio of the active components, which could not be varied by the healthcare professional or user.

Additional problems arise where a multi-drug compound therapy is required, because many users cannot cope with having to use more than one drug delivery system or make the necessary accurate calculation of the required dose combination. This is especially true for users with dexterity or cognitive difficulties. In some circumstances it is also necessary to perform a priming procedure of the device and/or needle cannulae before dispensing the medicaments. Likewise, in some situations, it may be necessary to bypass one drug compound and to dispense only a single medicament from a separate reservoir.

Accordingly, there exists a strong need to provide devices and methods for the delivery of two or more medicaments in a single injection or delivery step that is simple for the user to perform. The above-mentioned problems may be overcome by providing separate storage containers for two or more active drug agents that are then only combined and/or delivered to the patient during a single delivery procedure. Setting a dose of one medicament may automatically fix or determine the dose of the second medicament (i.e. non-user settable). Moreover, the opportunity may be given for varying the quantity of one or both medicaments. For example, one fluid quantity can be varied by changing the properties of the injection device (e.g. dialing a user variable dose or changing the device's "fixed" dose). The second fluid quantity can be changed by manufacturing a variety of secondary drug containing packages with each variant containing a different volume and/or concentration of the second active agent. The user or healthcare professional would then select the most appropriate secondary package or series or combination of series of different packages for a particular treatment regime.

Our disclosure also provides a medicated module that has two needle guard assemblies that will lock in a covering or distal position after each is retracted one time. The user can separate the first guard assembly from the module after injection to expose a second injection needle and a second guard assembly. This prevents unintended reuse of the first injection needle and allows a user to split the primary medicament injection volume into two separate injections.

These and other advantages will become evident from the following more detailed description of the invention.

One problem to be solved is to provide a medicated module and a drug delivery device where the administration of a medicament is improved.

SUMMARY

The disclosed medicated module and drug delivery device allows complex combinations of multiple drug compounds within a single drug delivery system. In particular, the user may be enabled to set and dispense a multi-drug compound device through one single dose setting mechanism and a single dispense interface. This single dose setter expediently controls the mechanism of the device such that a predefined combination of the individual drug compounds is delivered when a single dose of one of the medicaments is set and dispensed through the single dispense interface.

By defining the therapeutic relationship between the individual drug compounds our delivery device may help to ensure that a patient/user receives the optimum therapeutic combination dose from a multi-drug compound device without the inherent risks associated with multiple inputs where the user has to calculate and set the correct dose combination every time they use the device. The medicaments can be fluids, defined herein as liquids or gases or powders that are capable of flowing and that change shape at a steady rate when acted upon by a force tending to change its shape. Alternatively, one of the medicaments may be a solid that is carried, solubilized or otherwise dispensed with another fluid medicament.

The disclosed medicated module and drug delivery device may be of particular benefit to users with dexterity or cognitive difficulties as the single input and associated predefined therapeutic profile removes the need for them to calculate their prescribed dose every time they use the device and the single input allows considerably easier setting and dispensing of the combined compounds.

In a preferred embodiment a master drug compound, such as insulin, contained within a multiple dose, user selectable device could be used with a single use, user replaceable, module that contains a single dose of a second medicament and the single dispense interface. When connected to the primary device the secondary compound is activated/delivered on dispense of the primary compound. Although this disclosure specifically mentions insulin, insulin analogs or insulin derivatives, and GLP-1 or GLP-1 analogs as two possible drug combinations, other drugs or drug combinations, such as an analgesics, hormones, beta agonists or corticosteroids, or a combination of any of the above-mentioned drugs could be used.

The term "insulin" shall mean insulin, insulin analogs, insulin derivatives or mixtures thereof, including human insulin or a human insulin analogs or derivatives. Examples of insulin analogs are, without limitation, Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin or Des(B30) human insulin. Examples of insulin derivatives are, without limitation, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

As used herein the term "GLP-1" shall mean GLP-1, GLP-1 analogs, or mixtures thereof, including without limitation, exenatide (Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys- Asn-Gly-Gly-Pro-Ser-Ser-Gly-Ala-Pro-Pro-Pro-Ser-NH$_2$), Exendin-3, Liraglutide, or AVE0010 (H-His-Gly-Glu-Gly-Thr-Phe-Thr-Ser-Asp-Leu-Ser-Lys-Gln-Met-Glu-Glu-Ala-Val-Arg-Leu-Phe-Ile-Glu-Trp-Leu-Lys-Asn-Gly-Gly-Pro-Ser-Ser-Gly-Ala-Pro-Pro-Ser-Lys-Lys-Lys-Lys-Lys-Lys-NH$_2$).

Examples of beta agonists are, without limitation, salbutamol, levosalbutamol, terbutaline, pirbuterol, procaterol, metaproterenol, fenoterol, bitolterol mesylate, salmeterol, formoterol, bambuterol, clenbuterol, indacaterol.

Hormones are for example hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

According to one aspect, a medicated module is provided. The medicated module may be, preferably releasably, attachable to a drug delivery device. The medicated module may be demountable. The medicated module may form a demountable, multipart assembly for the drug delivery device. In particular, the medicated module may comprise a plurality of members, which may be removably connected to each other for demounting the medicated module. The drug delivery device may comprise a primary reservoir. The primary reservoir may contain a first medicament, preferably a plurality of doses of the first medicament. The medicated module may comprise a secondary reservoir. The secondary reservoir of the medicated module may comprise a dose, preferably a single dose, of a second medicament. In particular, the secondary reservoir may be filled with the second medicament before the medicated module is attached to the drug delivery device. Preferably, the secondary reservoir is a capsule that is contained in a, preferably rotatable, inner housing of the medicated module. The medicated module may be a medicated needle. The medicated module may comprise a first or distal needle cannula. The medicated module may comprise a second or proximal needle cannula. The secondary reservoir may be arranged in the axial direction between the first and the second needle cannula. The distal end of the distal needle cannula may be configured for being applied to an injection site. The proximal end of the distal needle cannula may be configured for piercing the secondary reservoir, in particular a seal or septum arranged at the distal end of the secondary reservoir. The distal end of the proximal needle cannula may be configured for piercing the secondary reservoir, in particular a seal or septum arranged at the proximal end of the secondary reservoir. The proximal end of the proximal needle may be configured for piercing the primary reservoir, in particular a seal or septum arranged at the distal end of the primary reservoir. Furthermore, the distal end of the proximal needle cannula may be configured for being applied to the injection site. The medicated module may comprise a first needle guard assembly and a second needle guard assembly. The respective needle guard assembly may be adapted and arranged to provide protection of the first and the second needle cannula arranged in a respective portion of the medicated module. The needle guard assembly may be removably connected to the second needle guard assembly, The respective needle guard assembly, in particular each needle guard assembly, may be configured to move in an axial direction only during, preferably direct, application of the respective needle guard assembly to an injection site. More specifically, the second needle guard assembly may be activated, in particular may be moveable in an axial direction, only once the first needle guard assembly has been used and removed from the module.

The medicated module may comprise a first housing and a second housing. The first needle guard assembly may be operably connected to the first housing. The second needle guard assembly may be operably connected to the second housing. Accordingly, the housing, in particular the first housing and the second housing, may be understood as a multipart assembly comprising the first and the second needle guard assembly, respectively. The second housing, preferably a proximal end of the second housing, may be configured for attachment to the drug delivery device. The second housing may have a connector. The connector may be arranged at the proximal end of the second housing. The connector may be configured for attaching the second housing, preferably the proximal end of the second housing, to the device. The second housing, preferably a distal end of the second housing, may be removably connected to the first housing. In particular, the first needle guard assembly may be removably connected to the second needle guard assembly due to the removable connection of the first and second housing. Accordingly, the medicated module may be understood as a demountable assembly for the drug delivery device, as described above. According to an embodiment, the secondary reservoir is arranged in the first housing. The first needle cannula may be mounted in the first housing. The second needle cannula may be mounted in the second housing.

The medicated module, preferably the previously mentioned inner housing, may comprise an unlock feature. The unlock feature may be operably connected to the second needle guard assembly that is activated after dispensing the dose, preferably the single dose, of the second medicament. The unlock feature may be adapted and arranged for enabling unlocking the first housing and, hence, the first needle guard assembly, from the second housing and, hence, the second needle guard assembly. Accordingly, the first needle guard assembly may be removable from the second needle guard assembly. In this way, dispensing of a dose of the first medicament from the drug delivery device via the proximal needle, which is still sterile after having dispensed the second medicament along with a dose of the first medicament, may be enabled. The medicated module preferably has a seal, tab, label, or other removable segment operably connected to the first and second housings to allow a user to remove the seal and separate, in particular unlock, the first housing, which is operably connected to the first needle guard assembly, from the second housing, which is operably connected to the second needle guard assembly, in particular after having dispensed a dose, preferably a single dose, held in the secondary reservoir. According to an embodiment, there is a lock-out feature. The lock-out feature may prevent the first housing from being removed until the second medicament has been dispensed through the first needle cannula.

According to an embodiment, the first housing contains a priming cavity. The priming cavity may be configured to accept and/or collect primed medicament from a primary reservoir contained in a drug delivery device when the module is attached thereto. The volume of the cavity may be fixed and may be designed to hold multiple priming volumes, preferably less than 50 micro liters. The priming cavity may also have a priming indicator, such as a window or other visual indicia, to allow the user to visually observe the presence of primed primary medicament in the cavity.

The reservoir contained in the medicated module, in particular the secondary reservoir, can be positioned in a rotatable member or inner housing. The rotatable member or inner housing may be operably connected to the first needle guard assembly. In this manner, when the first guard is retracted, the secondary reservoir, which is in fluid communication with a first needle cannula, may be placed in fluid communication with a second needle cannula because the retracting guard causes the inner housing to rotate and move in a proximal axial direction to engage the second needle with the secondary reservoir. Accordingly, when the first needle guard assembly is retracted in the proximal direction, the first and second needle cannulae may be in fluid communication with the medicament. When the first needle guard is fully extended in the distal direction only the first needle cannula may be in fluid communication with the secondary reservoir. The inner housing can also have a third position that it may occupy after the first guard begins to extend outwardly in the distal direction, returning to its original position. This third position may move the secondary reservoir in a slight distal direction just enough that the second needle is withdrawn from fluid engagement with the interior of the secondary reservoir. This distal movement may cause the distal end of the second needle to lodge within an upper septum of the secondary reservoir. In this position the second needle may form a hydraulic lock with the septum. In this way, fluid flow within the second needle cannula may be prevented, thus preventing any further dispensing of the primary medicament with the first housing attached to the medicated module.

The first and second guard assemblies can each have a locking member. The respective locking member may be activated as the respective guard begins to extend back to its original position. The locking members, in particular mechanical cooperation of the locking members and the guard assemblies, may prevent the guard assemblies from moving axially after each guard is removed from an injection site. Once a user has performed a first injection using the single dose of medicament contained in the first housing of the module, the user may then remove the seal that holds the two module housings together. The first housing, the secondary reservoir, the first needle and the first needle guard assembly can now be safely discarded because the first guard is locked in a needle covering position. The user can now use the drug delivery device to prime and/or inject another dose of the primary medicament through the second needle housing or module.

Locking of the two needle guard assemblies after axial movement can be accomplished in many ways that are known to the art. However, a preferred method includes the use of one or more moving or sliding locks contained within the module. The moving locks are configured such that when the guards are retracted they pick up the moving locks and move them to a position that prevents the guards from retracting in a proximal direction. Preferably the moving lock is a "circlip" type design having two or more components that are initially positioned in one part of the module housing and then are moved or slid distally by the guard as it retracts to a second position where the circlip locks into the module housing or other stationary structure to prevent further axial movement of the guard.

A single dose of the second medicament may be contained within the secondary reservoir of the medicated module. The medicated module preferably is configured as a sealed capsule containing the single dose of the second medicament. With a single activation of the dose button medicament from the primary reservoir and the second medicament from the capsule can be expelled through the dispense interface. When the first needle guard is in a down position, in particular when the first needle guard is fully extended in the distal direction, the connected drug delivery device can be primed with primary medicament contained in the drug delivery device such that none of the second medicament is dispensed through the outlet needle cannula, e.g. the first needle cannula. In one embodiment, as discussed above, the primed medicament is collected in a cavity of fixed volume. In a second embodiment, the medicated module comprises a bypass. The bypass may comprise a fluid path bypassing the reservoir of the medicated module. In particular, the bypass feature may permit priming of first/primary medicament contained in the attached drug delivery device at any volume, without dispense of the second medicament. The bypass can be any fluid flow path or channel that allows for delivery through the outlet needle of only the primary medicament. This type of bypass could be achieved by a number of means designed such that the primary medicament can flow to the outlet needle without interacting with the medicament contained within the secondary reservoir within the medicated module. When the first needle guard assembly is fully extended in the distal direction, the two needle cannulae may not be in fluid communication with the second medicament. Accordingly, when the first needle guard assembly is fully extended in the distal direction, the needle cannulae may be in fluid communication with the bypass.

When the first needle guard is retracted, in particular when the first needle guard is moved in the proximal direction into the first module housing, it may interact with an inner housing in the first housing of the module. Preferably, this inner housing contains the secondary reservoir of second medicament. As the first guard retracts, it may force the inner housing in a proximal direction causing the needle cannula mounted in the second (proximal) housing to pierce an upper septum in the secondary reservoir or capsule. Accordingly, when the first needle guard is retracted in the proximal direction, the first and second needle cannulae are now in fluid communication with the secondary reservoir and, hence, with the single dose of the second medicament. Accordingly, the flow path is through the module reservoir or secondary reservoir. The module may stay in this position until the needle guard is retracted, at which point the axial force exerted by the first needle guard may be diminished and the inner housing may move axially in a distal direction to a third position. In the third position, the proximal needle may be retracted slightly from the secondary reservoir and may lodge in a septum sealing the secondary reservoir, essentially blocking or plugging the needle outlet, thus creating a hydraulic lock. The hydraulic lock may prevent the user from dispensing any further amount of the primary medicament and the locked first needle guard may prevent a second use of the first needle cannula.

According to one aspect, a drug delivery device is provided comprising the previously described medicated module and a primary reservoir, the primary reservoir holding at least one dose, preferably a plurality of doses, of a further medicament.

According to a preferred embodiment, the medicated module is attachable to a drug delivery device. The medicated module comprises a first housing and a second housing, where the second housing has a proximal end having a connector configured for attachment to the drug delivery device and a distal end that is removable connected to the first housing. The medicated module comprises a reservoir in the first housing comprising a single dose of a medicament. The medicated module comprises a first needle guard assembly operably connected to the first housing and a second needle guard assembly operably connected to the second housing, where both guards are configured to move in an axial direction when applied to an injection site.

The present disclosure also relates to a drug delivery system, in particular a drug delivery device, to deliver two or more medicaments operable through a single dose setter and a single dispense interface, comprising, a housing containing a single dose setter operably connected to a primary reservoir of medicament containing at least one drug agent and a dose button operably connected to the primary reservoir of medicament. The system may also have a single dispense interface configured for fluid communication with the primary reservoir and a medicated module.

According to a preferred embodiment, a medicated module is provided, the medicated module being attachable to a drug delivery device. The drug delivery device comprises a primary reservoir of a first medicament and the medicated module comprises a secondary reservoir comprising a dose of a second medicament. The medicated module, in particular the secondary reservoir, may be pre-filled with the second medicament when the medicated module is attached to the device, in particular before fluid communication is established between the secondary reservoir and at least one of the first and the second needle cannula. The drug delivery device, in particular the primary reservoir, is preferably filled with first medicament before the module is attached to the device. The medicated module comprises a first needle guard assembly and a second needle guard assembly. The respective needle guard assembly is adapted and arranged to provide protection of a first and a second needle cannula arranged in a respective portion of the medicated module. The first needle guard assembly is removably connected to the second needle guard assembly. Each needle guard assembly is configured to move in an axial direction when the respective needle guard assembly is applied to an injection site. In particular, the second needle guard assembly may be applied to the injection site after removal of the first needle guard assembly.

The medicated module may be configured for fluid communication with the primary reservoir and comprises two module housings, each having a lockable needle guard. The user can separate the housings from each other by removing a seal or other removable connection means. There is a secondary reservoir in the module housing comprising a single dose of a second medicament. The two guard assemblies are configured to move in an axial direction during separate application to injection sites. Upon retraction of the first guard, the secondary reservoir becomes fluidly connected with the needle cannula that is in fluid communication with the primary medicament in the delivery device. The second needle guard assembly may be adapted and arranged to be attached to an injection side and, hence, to move in an axial direction only after the first needle guard assembly was removed from the medicated module.

With a single activation of the dose button, when the first guard is retracted, e.g. moved in the proximal direction, the medicament from the primary reservoir and the second medicament from the medicated module can be expelled through the needle cannula mounted in the first module housing. Upon completion of the delivery procedure, substantially all of the second medicament has been expelled as well as the selected dose of the first medicament through the single dispense interface. By "substantially all" we mean that at least about 80% of the second medicament is expelled from the drug delivery device, preferably at least about 90% is expelled. Additionally, if more of the primary medicament needs to be injected, the user can remove the first module housing, set another dose, and perform the injection using the second needle cannula and second needle guard assembly.

The medicated module can be designed for use with any drug delivery device with an appropriate compatible interface. However, it may be preferable to design the module in such a way as to limit its use to one exclusive primary drug delivery device (or family of devices) through employment of dedicated or coded features to prevent attachment of a non-appropriate medicated module to a non-matching device. In some situations it may be beneficial to ensure that the medicated module is exclusive to one drug delivery device while also permitting the attachment of a standard drug dispense interface to the device. This would allow the user to deliver a combined therapy when the module is attached, but would also allow delivery of the primary compound independently through a non-medicated drug dispense interface in situations, such as, but not limited to, dose splitting or top-up of the primary compound.

The medicated module makes it expediently possible to tailor dose regimes when required, especially where a titration period is necessary for a particular drug. The medicated module could be supplied in a number of titration levels with obvious differentiation features such as, but not limited to, aesthetic design of features or graphics, numbering etc, so that a patient could be instructed to use the supplied medicated module in a specific order to facilitate titration. Alternatively, the prescribing physician may provide the patient with a number of "level one" titration medicated modules and then when these were finished, the physician could then prescribe the next level. A key advantage of this titration program is that the primary device remains constant throughout.

In a preferred embodiment, the primary drug delivery device is used more than once and therefore is multi-use. However, the drug delivery device may also be a single use disposable device. Such a device may or may not have a replaceable reservoir of the primary drug compound, but the present disclosure is equally applicable to both scenarios. The device may be suitable to set and dispense a dose of the first medicament before the medicated module is attached to the device or after the medicated module was removed from the device. Accordingly, the device may be suitable to form a stand-alone device, configured to operate also in absence of the medicated module, for example. For this purpose, a needle cannula may be, preferably removably, attachable to the distal end of the device.

It is also possible to have a suite of different medicated modules for various conditions that could be prescribed as one-off extra medication to patients already using a standard drug delivery device. Should the patient attempt to reuse a previously used medicated module, the locking needle guard may be activated after a single use. Other means of alerting the user may include some (or all) of the following:

- Physical prevention of medicated module re-attachment to the primary drug delivery device once the module has been used and removed.
- Physical/hydraulic prevention of subsequent liquid flow through the drug dispense interface once it has been used.
- Physical locking of the dose setter and/or dose button of the primary drug delivery device.
- Visual warnings (e.g. change in color and/or warning text/indicia within an indication window on the module once insertion and/or fluid flow has occurred).
- Tactile feedback (presence or absence of tactile features on the outer surface of the module hub following use).

A further feature of this embodiment may be that both medicaments are delivered via one injection needle and in a single injection step. This offers a convenient benefit to the user in terms of reduced user steps compared to administering two separate injections. This convenience benefit may also result in improved compliance with the prescribed therapy, particularly for users who find injections unpleasant or who have cognitive or dexterity difficulties.

These as well as other advantages of various aspects of the present invention will become apparent to those of ordinary skill in the art by reading the following detailed description, with appropriate reference to the accompanying drawings.

The scope of the invention is defined by the content of the claims. The invention is not limited to specific embodiments but comprises any combination of elements of different embodiments. Moreover, the invention comprises any combination of claims and any combination of features disclosed by the claims.

BRIEF DESCRIPTION OF THE DRAWINGS

Exemplary embodiments are described herein with reference to the drawings, in which.

DETAILED DESCRIPTION

Figure 1:
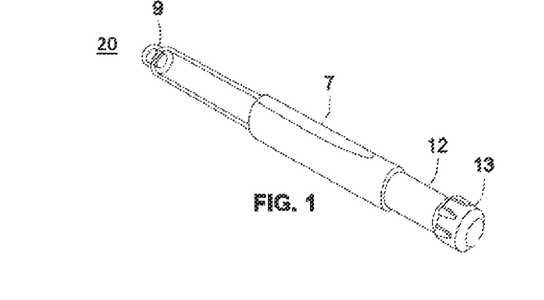
FIG. 1 illustrates one possible drug delivery device.

Specific embodiments of the disclosed medicated module enable administering a fixed predetermined dose of a secondary drug compound (medicament) and a variable dose of a primary or first drug compound through a single output or drug dispense interface. Setting the dose of the primary medicament by the user is independent of a single dose of a second medicament, which preferably is contained in a reservoir in a medicated module that is attachable to a drug delivery device. In a preferred embodiment, the drug dispense interface is a needle cannula (hollow needle). FIG. 1 illustrates one example of a drug delivery device 7 where the medicated module 4 (see FIGS. 2-11) can be attached to a connection means 9 of the distal end 20 of device 7, as shown in FIG. 1. Each medicated module 4 is preferably self-contained and provided as a sealed and sterile disposable module that has an attachment means 8 (see FIG. 3). Attachment means 8 is compatible to the attachment means 9 at the distal end 20 of device 7. Although not shown, the medicated module 4 could be supplied by a manufacturer contained in a protective and sterile container, where the user would peel or rip open a seal or the container itself to gain access to the sterile medicated module 4. In some instances it might be desirable to provide two or more seals for each end of the medicated module 4.

Figure 3:
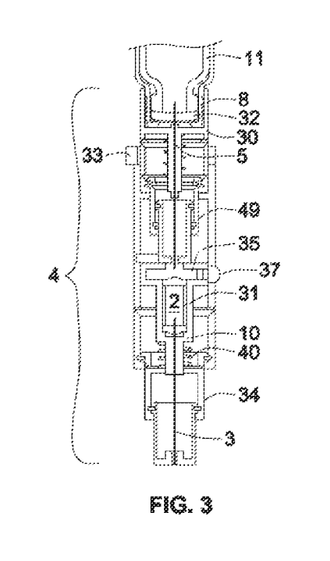
FIG. 3 illustrates a cross sectional view of the embodiment of the medicated module of FIG. 2 where the medicated module is attached to a drug delivery device.

Any known attachment means 8 can be used to attach the medicated module 4 to the chosen drug delivery device 7, including all types of permanent and removable connection means, such as threads, snap locks, snap fits, luer locks, bayonet, snap rings, keyed slots, and combinations of such connections. FIG. 3 illustrates the attachment means 8 as a thread that would engage like threads 9 of the distal end 20 of drug delivery device 7. The embodiments shown in the figures have the benefit of the second medicament 2 as a single dose being contained entirely within reservoir or capsule 31 of medicated module 4, hence minimizing the risk of material incompatibility between the second medicament 2 and the materials used in the construction of the medicated module 4, specifically an inner housing 10 or any of the other parts used in the construction of the module 4. The medicated module 4 comprises two needle cannulae 3, 5. The first needle cannula 3 is arranged at the distal end of the module 4. The second needle cannula is arranged proximally from the first needle cannula 3. The reservoir or capsule 31 is axially arranged between the needle cannulae 3, 5. The first and the second needle cannulae 3, 5 are positioned to establish fluid communication with the reservoir or capsule 31.

To minimize the residual volume of the second medicament 2, caused by recirculation and/or stagnant zones, that might remain in capsule 31 at the end of the dispense operation, it is preferable to use a flow distribution system, preferably contained within a portion of capsule 31. The secondary medicament 2 and flow distributor can be sealed with septa 6a and 6b (see FIG. 4), which can be fixed to the capsule 31 using ferrules, however, any type of seal could be used. Preferably the ferrules are made from a crimpable material, most preferably a metal, such as aluminum. The design of flow distributor system should ensure that at least about 80% of the second medicament 2 is expelled from capsule 31 through the distal end of the needle 3. Most preferably, at least about 90% should be expelled. Ideally, displacement of the first/primary medicament from the primary reservoir or cartridge 11 through the capsule 31 will displace the second medicament 2 without substantial mixing of the two medicaments.

Attachment of the medicated module 4 to the multi-use device 7 causes the engagement of the needle 5 mounted in a second housing 30 at the proximal end of module 4 to penetrate a septum 32 sealing the distal end of cartridge 11 of the multi-use device 7. Hence, the cartridge 11 is introduced in the device 7 before the module 4 is attached to the device 7. The cartridge 11 of the device 7 is filled with a first medicament before it is attached to the device 7. The capsule 31 of the module 4 is pre-filled with secondary medicament 2 before it is attached to the device 7. The first housing 21 is removably connected to second housing 30 through a removable seal 33. Accordingly, the medicated module 4 may be understood as a demountable assembly for the device 7. The seal 33 can be any structure where a user can pull or peel or twist the first housing 21 away from second housing 30. Once the engagement needle 5 has passed through the septum 32 of cartridge 11, fluid connection is made between the first medicament and the needle 5. At this point, the system can be primed or the dose of the multi-use device 7 set using a dose setter 12 (see FIG. 1) in the normal manner (e.g. by dialing out the appropriate number of units or cocking the device if only a single dose is possible). When a first needle guard 34 of medicated module 4 is retracted, e.g. moved in the proximal direction, for example by placing it on the injection site, then dispense of the medicaments is achieved by subcutaneously injecting the medicaments via activation of a dose button 13 on device 7. The dose button 13 can be any triggering mechanism that causes the dose of the first medicament that was set by the dose setter to move towards the distal end 20 of the device 7. In a preferred embodiment, the dose button 13 is operably connected to a spindle that engages a piston in the primary reservoir 11 of the first medicament.

One embodiment of the medicated module 4 is illustrated in FIGS. 2-9. In these embodiments, the medicated module 4 contains a discrete secondary reservoir or capsule 31 containing a fixed single dose of a second medicament 2. In some cases, this second medicament 2 may be a mixture of two or more drug agents that can be the same or different from the primary drug compound contained in cartridge 11 in the drug delivery device 7. Preferably, the capsule 31 is permanently fixed contained within the medicated module 4 and is designed to administer a fixed predetermined dose of the second medicament 2. However, in some cases, it may be preferred to design the module 4 such that the capsule 31 can be removed when empty and replaced with a new capsule. Likewise, a new injection needle may replace a used needle.

In the embodiments shown, capsule 31 has ends that are sealed with pierceable membranes or septa 6a and 6b that provide a hermetically sealed and sterile reservoir for the second medicament 2. The primary or engagement needle 5 can be fixed in the second housing 30 of the module 4 and configured to engage capsule 31 when the first needle guard assembly 34 is retracted into first housing 21. The output or distal needle 3 is preferably mounted in an inner housing 10 contained within first housing 21. Output needle 3 is in fluid communication with capsule 31 before the first needle guard assembly 34 is fully retracted.

Figure 4:
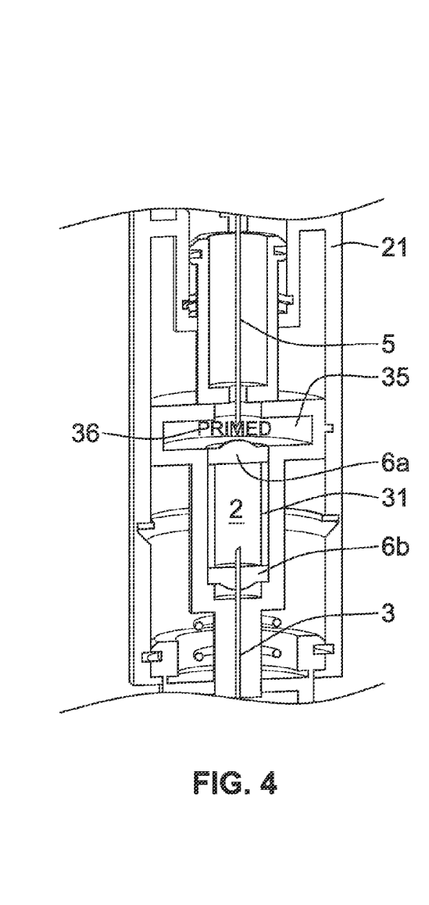
FIG. 4 illustrates a close up view of a portion of FIG. 3 to illustrate the cavity that accepts the primed medicament.

During use, attachment of the medicated module 4 to a multi-use device, such as the one shown in FIG. 1, causes the primary needle 5 to pierce septum 32 of cartridge 11 contained in the device 7. When first attached to the delivery device 7 and before the first needle guard assembly 34 is activated (see FIG. 3), the primary needle 5 is in fluid communication with cavity 35. This cavity 35 is designed and configured to accept primary medicament used to prime the device 7 before use. The cavity 35 preferably has a window 37 that allows the user to visually observe that that the primed medicament has entered the cavity 35. Most preferably, window 37 incorporates a lens and/or writing 36 that becomes more clearly visible due to refraction changes when the cavity 35 fills with primed medicament. For example, as shown in FIG. 4 the words "PRIMED" would initially be out of focus and non-legible before primed medicament is added to the cavity 35 and then becomes in focus as the primed medicament fills the cavity 35.

Figure 5:
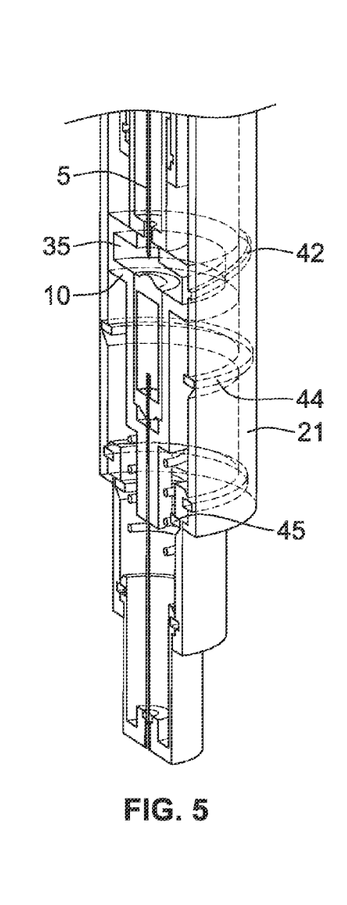
FIG. 5 illustrates the starting position of the medicated module of FIG. 3.
Figure 6:
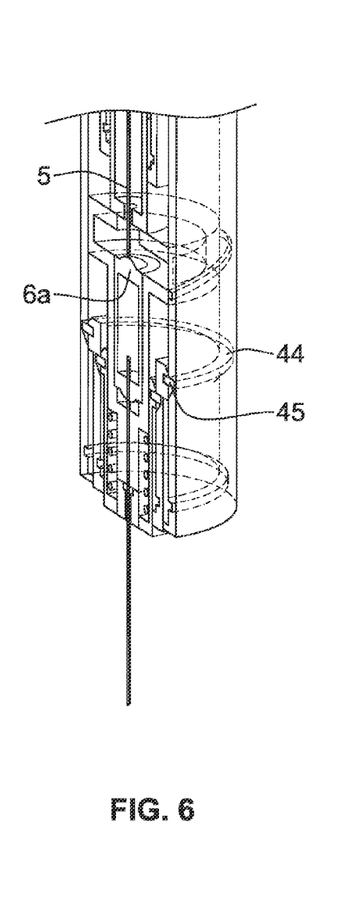
FIG. 6 illustrates the injection position of the medicated module of FIG. 3.
Figure 7:
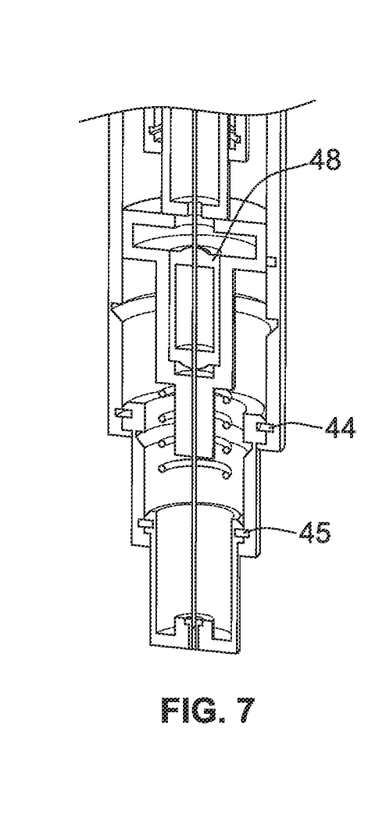
FIG. 7 illustrates the ending position of the medicated module of FIG. 3.
Figure 8:
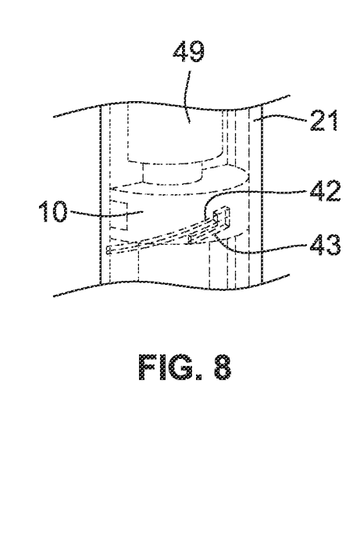
FIG. 8 illustrates a close-up view of the inner housing of the first module housing that contains the reservoir.

FIGS. 5-7 show a cutaway view of the medicated module 4 prior to injection, in an injection position, and a final locked position. As mentioned, prior to the retraction of the first needle guard assembly 34, needle 5 is not in communication with reservoir 31, but instead with cavity 35. As the first needle guard 34 is retracted, shown as a two-piece guard, a biasing member or spring 40 exerts a proximal force on inner housing 10. This causes inner housing 10 to follow a helical path defined by a pin and groove combination 42 that is positioned between the outer surface of the inner housing 10 and the inner surface of the first housing 21. FIG. 8 shows a close-up view of this pin and groove combination, however, in alternative embodiment the pin and groove could be reversed. This movement of the inner housing 10 in the proximal direction causes the reservoir/capsule 31 to likewise move and, thus, causes needle 5 to pierce septum 6a as shown in FIG. 6. In this injection position, both needle cannulae 3, 5 are in fluid communication with medicament 2 contained in capsule 31. Also, in this injection position, the first needle guard assembly 34 has picked-up or engaged moving locks, shown as circlips 44 and 45.

As the user removes the drug delivery device 7 from the injection site, spring 40 causes the first guard assembly 34 to expand back to its original extended position as shown in FIG. 7. Moving locks 44 and 45 are carried with the expanding needle guard 34 and eventually engage (snap into) grooves thereby locking the first needle guard assembly 34 from further axial movement. Additionally, as the biasing force on inner housing 10 is diminished it begins to reverse its helical path dictated by the pin and groove combination 42, except that it will follow a second and shorter helical path 43 to rest in a third position. This secondary path is configured such that the inner housing 10 moves distally only enough that needle 5 is retracted from the interior of capsule 31 but not enough that it completely exits septum 6a. Preferably, the distal end or outlet opening of needle 5 should remain embedded in septum 6a thus establishing a hydraulic lock 48 that seals and prevents further dispense of first medicament from cartridge 11. In this final position, the needle guard 34 is locked covering the used needle 3 and the entire drug delivery system is also hydraulically locked to prevent further dispense of first medicament.

Figure 9:
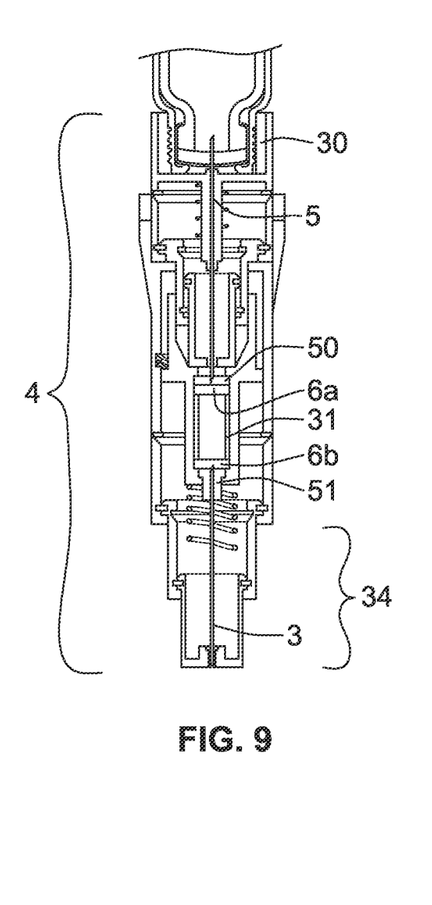
FIG. 9 illustrates a cross sectional view of another embodiment where a bypass is present in place of the priming cavity.

An alternative embodiment is shown in FIG. 9 where the cavity 35 in inner housing 10 is replaced with bypass 50. In the starting position as shown, capsule 31 is not in fluid communication with either needle cannulae 3 or 5. Many possible designs of the capsule 31 can allow for this initial position, including the use of support features, such as bellow type structures that keep the capsule 31 suspended in the inner housing 10 to avoid penetration by needles 3 and 5 until required. In this non-collapsed or suspended state, the first medicament can flow from needle 5 around capsule 31, through bypass 50, and out of needle 3. Flow around or bypassing capsule 31 is accomplished by configuring the capsule 31 to have one or more vanes or channels down the outside of the capsule 31. Alternatively, the internal walls of the inner housing 10 could have these vanes or fluid channels incorporated therein and then the outer walls of the capsule 31 could be smooth. When the first needle guard assembly 34 retracts, needle hub 51 moves proximally, causing the proximal end of needle 3 to engage septum 6b. Needle hub 51 also forces capsule 31 to move proximally causing the distal end of needle 5 to pierce septum 6a. When the first needle guard 34 is fully retracted both needle cannulae 3, 5 are then in fluid communication with the medicament 2 in capsule 31.

Figure 2:
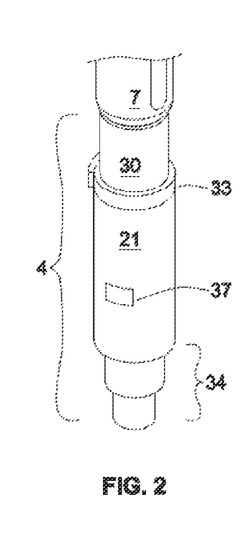
FIG. 2 illustrates an embodiment of the medicated module having two housings, where the second housing is attached to a drug delivery device as shown in FIG. 1.
Figure 10:
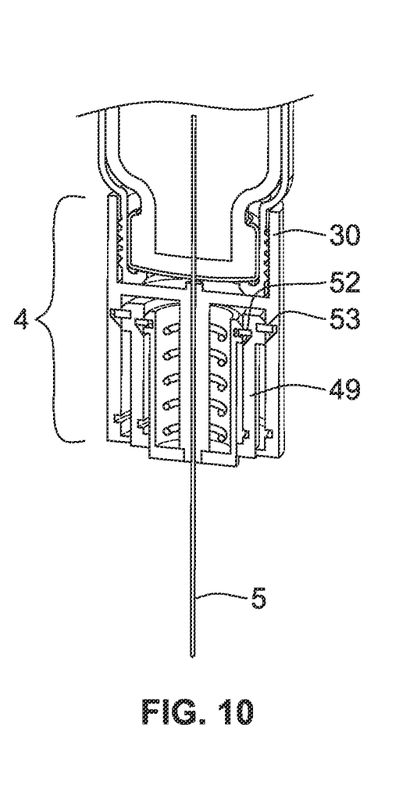
FIG. 10 illustrates a cross sectional view of the second module housing during injection after removal of the first module housing.
Figure 11:
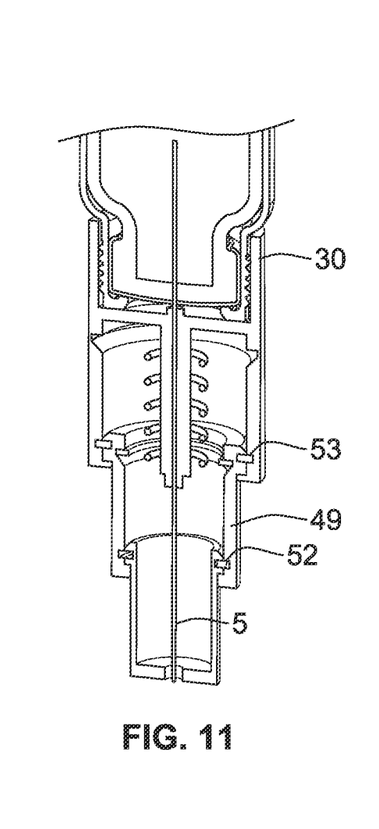
FIG. 11 illustrates a cross sectional view of the second module housing after injection with the second needle guard locked.

If the user requires an additional injection of the first medicament, the user can remove seal 33 (see FIG. 2). By doing so, the first housing 21, including first needle guard assembly 34, inner housing 10, capsule 31, and needle 3, can be removed from second housing 30 to expose and, hence, to activate, the second needle guard assembly 49. FIG. 10 shows module 4 with the housing 21 removed leaving only second housing 30 in place and with the second needle guard assembly 49 in a retracted (injection), e.g. proximal, position. Second needle guard assembly 49 is similarly configured as first needle guard assembly 34, including moving locks 52 and 53 that are picked-up by the retracted guard 49 and locked into position when the guard assembly 49 returns to its starting position (see FIG. 11). Although needle 5 was initially used to dispense the second medicament 2 in capsule 31 when the first housing 21 was still attached to module 4, the needle 5 did not come in contact with the user/patient, thus preserving sterility. As such, needle 5 can be safely used to perform a subsequent (second) injection of first medicament from cartridge 11. Once the module 4 is withdrawn from the injection site, the second guard 49 locks, completely covering needle 5 and no further injections are possible. Module 4 can then be removed from device 7 and safely discarded. An additional preferable feature is the inclusion of a second housing lockout where the second needle 5 cannot be accessed for a second injection until the medicament 2 in the capsule 31 has been dispensed from the first needle 3. This can be accomplished in a number of ways, but preferably occurs when the inner housing 10 is first rotated. This will help prevent a user from injecting only the first medicament and skipping the administration of the single dose of second medicament 2, either accidentally or deliberately.

The two guard assemblies 34, 49 could be any design that would prevent accidental needle sticks and/or reduce the anxiety experienced by users who suffer from needle phobia. The exact design of these guards is not critical to the present disclosure, however, a preferred design is one that prevents only a singe injection for each needle cannulae 3, 5. Proximal movement of the guard assemblies 34, 49 activates or loads a resilient or biasing member within the module housing, which preferably is a compression spring. As the guard reaches a trigger point in its proximal travel, it engages or picks up one or more sliding locks. The trigger point could be any point along the travel, preferably at the end of travel. For safety reasons, moving the trigger point to earlier in the travel could be beneficial to ensure that the locking system is triggered just prior to the point where the needle tip penetrates the patient.

Upon completion of the dose delivery and upon withdrawing the module 4 from the patient's injection site, the guards 34, 49 will reverse their axial path moving distally due to the force or reverse action of the resilient member. As the guards 34, 49 move distally they will carry one or more moving or sliding locks with them until the locks engage non-moving parts of module 4. Although a specific design of the moving lock is illustrated in FIGS. 5-7 and 10-11, any type of lock, whether moving or not, will work, for example a sliding o-ring or stationary flexible fingers or single use "retractable biro pen" type mechanism or pin following a groove could be used as long as the guard is locked in a needle covering position and prevents further use of the medicated module as a dose delivery tool.

In any of the above described embodiments, the second medicament 2 may be either in a powdered solid state, any fluid state contained within the secondary reservoir or microcapsule, or coated to the inside surface of the drug dispense interface. The greater concentration of the solid form of the medicament 2 has the benefit of occupying a smaller volume than the liquid having lower concentration. This in turn reduces the ullage of the medicated module 4. An additional benefit is that the solid form of the second medicament 2 is potentially more straightforward to seal in the secondary reservoir than a liquid form of the medicament 2. The device 7 would be used in the same manner as the preferred embodiment with the second medicament 2 being dissolved by the first medicament during dispense.

To minimize diffusion of the second medicament 2 contained in the capsule 31 within the medicated module 4 into the first medicament during dispense of the medicaments a flow distributor may be included in the capsule 31. This flow distributor also ensures efficient expulsion of the second medicament 2 from the system and greatly minimizes residual volume. One possible embodiment of the flow distributor is an annular pin. The annular pin can be positioned in the capsule 31 and configured such that the second medicament 2 fills flow channels that are defined by the shape and location of one or more support ribs. The flow distributor can be constructed of any material that is compatible to the first and second medicaments. A preferred material would be that typically used to manufacture septa or pistons (bungs) found in multi-dose medicament cartridges, although any material that is compatible with the medicament during long term storage would be equally applicable. The shape of the flow channels can be optimized for plug flow of medicament by varying the dimensions and geometry. The cross-sectional area of the annulus formed between the flow distributor and the wall of the capsule should be kept relatively small. The volume available to store the second medicament 2 would equal the internal volume of the capsule 31 minus the volume of the flow distributor. Therefore, if the volume of the flow distributor is marginally smaller than the internal volume of the capsule 31, a small volume is left which the second medicament 2 resides. Hence, the scale of both the capsule 31 and the flow distributor can be large while storing a small volume of medicament 2. A further benefit of this is that as the available volume for medicament 2 is defined by the difference in volumes between the flow distributor and its housing, the external capsule 31 geometry is not dictated by the volume of medicament 2. Resultantly for small volumes of second medicament 2 (e.g. 25 micro liters) the capsule 31 can be of an acceptable size for handling, transport, manufacture, filling and assembly.

The connection or attachment between the primary device 7 and the medicated module 4 of the above described embodiments may contain additional features (not shown), such as connectors, stops, splines, ribs, grooves, and the like design features, that ensure that specific medicated module 4 are attachable only to matching drug delivery devices 7. Such additional features would prevent the insertion of a non-appropriate medicated module 4 to a non-matching injection device.

The shape of the medicated module 4 may be a cylindrical body or any other geometric shape suitable for defining a fluid reservoir or for containing discrete self-contained reservoir of the second medicament 2 and for attaching one or more needle cannula 3, 5. The medicated module 4 can be manufactured from glass or other drug contact suitable material. The integrated injection needle 3 can be any needle cannula suitable for subcutaneous or intramuscular injection.

Preferably, the medicated module 4 is provided by a drug manufacturer as a stand-alone and separate device that is sealed to preserve sterility until to the point of use. The sterile seal of the module is preferably designed to be opened automatically, e.g. by cutting, tearing or peeling, when the medicated module is advanced or attached to the drug delivery device by the user. Features such as angled surfaces on the end of the injection device 7 or features inside the module 4 may assist this opening of the seal.

The medicated module 4 should be designed to operate in conjunction with a multiple use injection device 7, preferably a pen-type multi-dose injection device, similar to what is illustrated in FIG. 1. The injection device 7 could be a reusable or disposable device. By disposable device it is meant an injection device that is obtained from the manufacturer pre-loaded with medicament and cannot be reloaded with new medicament after the initial medicament is exhausted. The device may be a fixed dose or a settable dose and preferably a multi-dose device, however, in some cases it may be beneficial to use a single dose, disposable device.

A typical injection device contains a cartridge or other reservoir of medication. This cartridge is typically cylindrical in shape and is usually manufactured in glass. The cartridge is sealed at one end with a rubber bung and at the other end by a rubber septum. The injection device is designed to deliver multiple injections. The delivery mechanism is typically powered by a manual action of the user, however, the injection mechanism may also be powered by other means such as a spring, compressed gas or electrical energy. The injection device may further comprise a dose setter; the dose setter may be operably connected to the delivery mechanism. The injection device comprises a dose button; the dose button may be operably connected to the delivery mechanism. The dose button may be any triggering mechanism that causes the dose of the medicament that was set by the dose setter to move distally towards the distal end of the device. In a preferred embodiment, the dose button is operably connected to a spindle that engages a piston in the primary reservoir of the first medicament. In a further embodiment the spindle is a rotatable piston rod comprising two distinct threads.

Exemplary embodiments of the present invention have been described. Those skilled in the art will understand, however, that changes and modifications may be made to these embodiments without departing from the true scope and spirit of the present invention, which is defined by the claims.

We claim:

1. A medicated module attachable to a drug delivery device, the drug delivery device comprising a primary reservoir of a first medicament and the medicated module comprising a secondary reservoir comprising a dose of a second medicament, wherein the medicated module comprises:
    a first housing and a second housing, the second housing having an attachment means to attach the medicated module to the drug delivery device, wherein the secondary reservoir is arranged in the first housing;
    a distal needle cannula mounted in the first housing, wherein a distal end of the distal needle cannula is configured to be applied to an injection site;
    a proximal needle cannula mounted in the second housing, wherein a proximal end of the proximal needle cannula is configured for piercing the primary reservoir,
    wherein the distal and proximal needle cannulae are positioned to establish fluid communication with the secondary reservoir and wherein the secondary reservoir is arranged in an axial direction between the distal needle cannula and the proximal needle cannula,
    wherein the first housing is removably connected to the second housing, and wherein a distal end of the proximal needle cannula is configured for being applied to the injection site when the first housing is removed from the second housing;
    a first needle guard assembly operably connected to the first housing; and
    a second needle guard assembly operably connected to the second housing, the respective needle guard assembly being adapted and arranged to provide protection of the distal needle cannula and the proximal needle cannula, wherein each needle guard assembly is configured to move in an axial direction when the respective needle guard assembly is applied to the injection site,
    wherein the secondary reservoir and the proximal needle cannula form a hydraulic lock to prevent fluid flow when the first needle guard assembly is withdrawn from the injection site, and wherein a distal end of the proximal needle cannula is caused to lodge within an upper septum of the secondary reservoir such that the secondary reservoir and the proximal needle cannula form a hydraulic lock to prevent fluid flow.

2. The medicated module of claim 1, wherein the second needle guard assembly is adapted and arranged to move in an axial direction only after the first needle guard assembly is removed from the medicated module.

3. The medicated module according to claim 1, where the first housing has an inner housing containing a priming cavity which is configured to accept first medicament from the primary reservoir.

4. The medicated module according to claim 3, further comprising a priming indicator which is configured to allow a user to visually observe the presence of first medicament in the priming cavity.

5. The medicated module according to claim 3, where the inner housing is rotatable, and where the secondary reservoir is contained in the rotatable inner housing operably connected to the first needle guard assembly, and where the secondary reservoir is in fluid communication with the distal needle cannula and is placed in fluid communication with the proximal needle cannula when the first needle guard assembly causes the inner housing to rotate and move axially.

6. The medicated module according to claim 1, wherein the secondary reservoir is positioned in a rotatable remember, wherein the rotatable member is operably connected to the first needle guard assembly such that the distal and proximal needle cannulae are in fluid communication with the second medicament when the first needle guard assembly is retracted in a proximal direction.

7. The medicated module according to claim 1, where the first and second needle guard assemblies each have a locking member for preventing axial movement of the respective needle guard assembly.

8. The medicated module according to claim 1, where the medicated module contains a locking member, configured to prevent the first needle guard assembly from moving axially after the first needle guard assembly is removed from the injection site.

9. The medicated module according to claim 1, where the secondary reservoir contains a liquid medicament.

10. The medicated module according to claim 1, where the medicament in the secondary reservoir comprises a GLP-1 or comprises a premix of insulin and a GLP-1.

11. The medicated module according to claim 1, where the distal and proximal needle cannulae are not in fluid communication with the second medicament when the first needle guard assembly is fully extended in a distal direction.

12. The medicated module according to claim 1, where the secondary reservoir has a bypass which is configured for bypassing the secondary reservoir.

13. The medicated module of claim 12, where the distal and proximal needle cannulae are in fluid communication with the bypass when the first needle guard assembly is fully extended in a distal direction.

14. The medicated module according to claim 1, comprising an unlock feature operably connected to the second needle guard assembly to activate the second needle guard assembly after dispensing the dose of the second medicament, wherein the unlock feature is adapted and arranged for unlocking the first housing from the second housing.

15. A drug delivery system comprising a drug delivery device and the medicated module according to claim 1, wherein the drug delivery device contains a primary reservoir, the primary reservoir holding at least one dose of a first medicament.

* * * * *